(12) United States Patent
Rose, III et al.

(10) Patent No.: US 6,723,307 B2
(45) Date of Patent: Apr. 20, 2004

(54) COSMETIC LIP PRODUCT WITH SOUR FLAVOR

(75) Inventors: Albert C. Rose, III, Litchfield, OH (US); Barbara L. Cashmere, Bay Village, OH (US); Paul J. Breha, III, Seven Hills, OH (US); Janet W. Thompson, Avon Lake, OH (US)

(73) Assignee: Bonne Bell, Inc., Lakewood, OH (US)

( * ) Notice: Subject to any disclaimer, the term of this patent is extended or adjusted under 35 U.S.C. 154(b) by 0 days.

(21) Appl. No.: 10/075,219

(22) Filed: Feb. 14, 2002

(65) Prior Publication Data

US 2003/0157043 A1 Aug. 21, 2003

(51) Int. Cl.$^7$ .............................. A61K 6/00; A61K 7/00; A61K 7/025
(52) U.S. Cl. ........................................ 424/64; 424/401
(58) Field of Search ................... 424/64, 401

(56) References Cited

U.S. PATENT DOCUMENTS

| | | | |
|---|---|---|---|
| 4,551,332 A | | 11/1985 | Stillman |
| 4,829,092 A | | 5/1989 | Nelson et al. |
| 4,873,078 A | | 10/1989 | Edmundson et al. |
| 4,970,220 A | | 11/1990 | Chaussee |
| 5,776,441 A | * | 7/1998 | Scancarella et al. .......... 424/61 |
| 5,804,594 A | | 9/1998 | Murad |
| 5,833,998 A | | 11/1998 | Biedermann et al. |
| 5,856,364 A | * | 1/1999 | Martin ....................... 514/724 |
| 5,932,197 A | | 8/1999 | Arnaud |
| 5,939,085 A | * | 8/1999 | Jacobs et al. ................ 424/401 |
| 6,136,301 A | | 10/2000 | Pelle et al. |
| 6,203,809 B1 | | 3/2001 | Nichols |
| 6,224,888 B1 | | 5/2001 | Vatter et al. |

* cited by examiner

*Primary Examiner*—James M. Spear
*Assistant Examiner*—S. Howard
(74) *Attorney, Agent, or Firm*—Fay, Sharpe, Fagan, Minnich & McKee, LLP

(57) ABSTRACT

Methods for making a sour tasting cosmetic lip product containing one or more acids dissolved in a base composition, and the products formed thereby, are disclosed. The products possess a pleasing sour taste while not producing irritation or burning on the lips or mouth. Ingredients such as sunblocks, moisturizers and vitamins may be added to the compositions depending on the properties desired in the final product. The compositions according to the present invention comprise from about 2% to about 25% by weight acid and are preferably anhydrous.

24 Claims, No Drawings

COSMETIC LIP PRODUCT WITH SOUR FLAVOR

FIELD OF INVENTION

The present invention relates to cosmetic and therapeutic compositions for the lips containing one or more acids. More particularly, the present invention relates to lip compositions comprising an acid that exhibit a sour taste.

BACKGROUND OF THE INVENTION

Unprotected skin is very susceptible to drying out and becoming irritated from exposure to the elements. This is especially true with regard to the lips, which have been found to be even more vulnerable to water loss than typical skin. This is due, in part, to the fact that the lips have a thinner stratum corneum, the outermost of three layers comprising skin, and contain a lesser amount of lipids than skin on other parts of the body. When the lipid barrier is depleted or inadequate, lips dry out, becoming irritated and prone to cracking. Lips are susceptible to other harms as well. For example, due to the fact that lips contain less melanin than other areas of skin, they are at risk of sunburn and UV damage.

In response to this, there have been various products introduced by manufacturers to keep the lips in a moisturized, smooth condition and protected from damage. These products most typically contain waxes or oils that mitigate the amount of moisture that escapes from the lips into the atmosphere. Some products may additionally contain moisturizers as well as healing agents to actually replace the moisture that has been lost and/or sooth damaged lips. Various sunscreens are also added to some products to protect the lips from sun damage.

Although useful, the taste and/or consistency of these products often does not appeal to consumers, especially younger users in their adolescent and teenage years. These users often want a tasteful and long lasting lip product that can easily be reapplied as desired. It has been found that slightly sour tasting candies and other products are pleasant to many consumers and in great demand. One only need consider the great variety of sour tasting candy and beverages now on the market to realize this. These products are typically given their sour taste by incorporating a small amount of acid, typically one or more fruit acids, into the product formulation. These acids stimulate taste receptors mainly along the sides of the tongue that are sensitive to such compounds. The concentration of acid in these products must be carefully controlled, great enough such that a pleasant "tanginess" is provided, but not so great that the acid burns or irritates the mouth.

The use of some types of acids in skin products is known. For example, it is known to use various alpha-hydroxy acids in skin lotions and creams to accelerate skin cell turnover by chemically exfoliating the top layer of skin cells. (See, e.g., U.S. Pat. No. 5,939,085). These products, however, are designed to achieve practically the exact opposite result of the present invention. Whereas the present invention is designed as a humectant and moisturizer and uses a relatively small amount of acid as a gentle flavoring agent, the hydroxy acid containing products are used to treat acne and other skin conditions by removing the cells from the skin surface using an astrigent acid-based composition, in effect "burning off" the upper skin layer. The use of such products on the delicate skin of the lips would be extremely discomforting.

With the great demand for sour tasting products, a need exists for a sour tasting lip product that can easily be reapplied, will not irritate the lips when used as directed, can be formulated with various lip moisturizers and protectors, and that is relatively stable over extended periods of time.

SUMMARY OF THE INVENTION

The present invention provides a method for making a sour tasting lip product containing one or more acids dissolved in a base composition, and the products formed thereby. The acids used in the invention are generally any of the naturally occurring fruit acids, although other acids may also be used.

Anhydrous acids are first dissolved in a suitable solvent, such as propylene glycol, under heat and stirring. Preferably the solvent and other components of the composition are substantially anhydrous. As used herein, "substantially anhydrous" means containing less than about 5% water by weight. After the acid is fully dissolved, a suitable cosmetic lip base is added to the mixture. As used herein, "cosmetic base" refers to any cosmetically or pharmaceutically acceptable carrier or base composition suitable for use in lip glosses, lip balms, lipsticks, and other compositions appropriate for application on the lips and around mucous membranes. This base may contain any of a number of known ingredients, such as various oils, moisturizers, emollients, etc., in any concentration that does not adversely affect the properties of the final composition. Other components may also be added, such as vitamins, sweeteners and other flavorings, sunblock agents, colorants, etc. The final composition is mixed to form a homogenous composition of the desired consistency.

Depending on the type of flavoring added to the mixture, the final composition will typically have a tart, sour fruit taste. The content of the final composition is preferably about 2% to about 25% by weight acid, about 3% to about 25% solvent, about 1% to about 10% flavoring, and about 55% to about 85% cosmetic lip base. The final composition will preferably have a pH of about 2.00–4.00. Although the final composition may be formulated to have any consistency desired, the lip composition produced by the present invention will typically have a consistency similar to that of a heavy lotion or skin cream. Therefore it may easily be stored in small cosmetic bottles and applied to the lips using an applicator colloquially known as a "doe-foot" applicator. This type of applicator consists of a small absorbent tip on the end of a thin tubular body. The absorbent tip is dipped in the composition and then dabbed on the lips, transporting the composition from the tip to the lips.

DETAILED DESCRIPTION OF THE INVENTION

The present invention provides a process for producing sour tasting cosmetic lip products containing one or more acids dissolved in a cosmetic lip base composition, and the products formed from this process. Other ingredients may be incorporated into the lip products of the present invention, including, but not limited to, moisturizing aids, vitamins, and sunblocks.

The acids suitable for use in the present invention include any acid that will produce a stable mixture and a sour flavor when combined in specific concentrations with a cosmetic lip base composition, but, when combined in a final product, will not burn the lips or mouth even after heavy use. By "heavy use", the applicants are generally referring to continuous extended exposure of 24 hours or greater and/or repeated applications within that time. Preferably, the acids used in the present invention include one or more of the acids naturally occurring in various fruits, including but not limited to citric acid, malic acid, tartaric acid, fumaric acid, propionic acid, acetic acid, and lactic acid. These acids are weaker than some of the stronger mineral acids, such as hydrochloric acid, and produce a pleasing sour taste, especially when combined with complementary fruit flavorings in the final composition. Therefore, although other acids are contemplated by the invention, fruit acids will be used in all subsequent discussion for clarity and convenience. Similarly, while the subsequent discussion may refer to a single acid, it must be remembered that any combination of one or more fruit acids may be used in formulating a composition according to the present invention. A preferred formulation of acids for use in the present invention is citric acid or a combination of citric acid with one or more other fruit acids. Preferably, the total amount of acid in the final product is from about 2% to about 25% by weight, more preferably about 2% to about 15% by weight. In the case of the use of multiple acids, the combined amount of all such acids will fall within these concentration ranges. The final composition will typically have a pH of about 2.00–4.00, and preferably about 2.68–3.90. In the case of an anhydrous final composition, pH is measured on a 5% by weight aqueous solution of the composition.

The acids for use in the present invention are typically USP grade (99%+pure) and purchased in powder form. These acids are available from various companies such as Aldrich Chemical Co., Milwaukee, Wis. To produce more uniform mixing and promote better consistency in the final composition, the acid is preferably dissolved in a solvent prior to mixing with a cosmetic lip base. Suitable solvents include any solvents in which the selected powder acid is soluble and which are themselves soluble in the cosmetic lip base. Preferable solvents include compounds that allow for dissolution of the relatively polar acids while being easily incorporated themselves into the generally non-polar cosmetic base. Thus, preferred solvents include, but are not limited to glycerin, propylene glycol, dipropylene glycol, butylene glycol and its higher homologues. In addition to being somewhat sweet and thus enhancing the flavor of the final composition, these solvents readily dissolve the acids upon heating and are easily incorporated into a typical cosmetic lip base. A most preferred solvent is propylene glycol. The use of water as a solvent, although workable and contemplated by the invention, is not preferred, since the reactivity and stability of the acid in the final composition becomes more difficult to control, which may lead to a burning sensation on the lips and mouth. Preferably, the total amount of solvent in the final product is from about 3% to about 25% by weight, more preferably about 5% to about 20% by weight.

Suitable cosmetic lip bases for the present invention may include any compositions useful in cosmetic lip products that are compatible with the acid and solvent used in formulating the invention. Cosmetic bases in the present invention may include various ingredients that find use in lip glosses, lip balms, lipsticks, lip moisturizers, and other lip products in any concentration that does not adversely affect the sour flavoring and other properties of the final composition. Thus, ingredients suitable for use in the cosmetic bases of the present invention may include, but are not limited to, various oils, waxes, humectants, emollients, proteins, preservatives, antioxidants, emulsifiers, sunblocks, colorants, fragrances, moisturizers, healing agents and vitamins.

"Oils" as used herein encompass not only naturally occurring plant, animal and mineral oils, but also oil-like emollients such as fatty esters, fatty alcohols and silicone oils. Suitable moisturizers and oils include, but are not limited to, polybutene; lanolin; petrolatum; vegetable oil; mineral oil; castor oil; isopropyl palmitate; diisopropyl dimerate; glycerides, triglycerides and other esters; glycerols; diglycerols; olive oil; vitamin E acetate; and mixtures thereof.

"Waxes" as used herein encompass not only those plant, animal and mineral waxes containing esters of fatty acids and alcohols and saturated hydrocarbons, but also synthetic resins having a wax-like texture, such as silicone waxes. Suitable waxes include, but are not limited to, beeswax; paraffin wax; lanolin wax; jojoba wax; carnauba wax; spermaceti; ozokerite; candellila wax; animal wax; synthetic wax; plant and mineral waxes; and mixtures thereof.

Suitable healing agents or other active ingredients suitable for use in the present invention include, but are not limited to, aloe vera; elastin; collagen; vitamin E and derivatives thereof; vitamin C and derivatives thereof; vitamin A and derivatives thereof; allantoin; calamine; dimethicone; cocoa butter; shark liver oil; botanical extracts; phospholipids; and mixtures thereof.

Other materials suitable for use in the present invention and specific formulations are disclosed in "Cosmetics: Science and Technology", 2nd Ed., Vol. 1, Wiley Interscience, 1972, and "The Chemistry and Manufacture of Cosmetics", 2nd Ed., Vol. IV, chapter 44, M. G. DeNavarre, Continental Press, 1975, the disclosures of which are incorporated herein by reference.

Preferably, the cosmetic base will contain polybutene and mineral oil. The use of greater than negligible amounts of water in the cosmetic base, while contemplated, is not preferred, for the same reasons that water is not a preferred solvent, as stated above. Preferably, the total amount of cosmetic base in the final product is from about 55% to about 90% by weight, more preferably about 60% to about 85% by weight.

In addition to the acid, solvent, and cosmetic lip base, other ingredients may be added to the lip compositions of the present invention. These ingredients may be part of the cosmetic base, or they may be added separately. Typically, for ease of production, these ingredients are those components that are only desired in specific formulations of the present invention. The cosmetic base and other ingredients may be combined into a bulk base. In this way, only a single cosmetic base is needed, which can be used for all formulations, while those additional ingredients only desired in specific instances may easily be added or have their concentration changed without altering the cosmetic base. Representative ingredients that may typically be added to the composition separately from the cosmetic base include, but are not limited to, artificial and natural sweeteners, $TiO_2$, and artificial and natural flavorings.

In a preferred embodiment, an artificial sweetener or sugar by-product that exhibits a sweetness anywhere from 10 to 500 times greater than natural sugar is added to the composition as a flavor enhancer, along with one or more proprietary flavorings available from various sources. Although sugar may be used as a sweetener, a proprietary flavor enhancer is preferred since they generally exhibit better long-term stability and greater resistance to microbial buildup. A preferred sweetener for use in the present invention is "Flavor Enhancer", available from Noville, Inc.

$TiO_2$ is both a whitening agent and a sunblock and may be added in varying amounts, depending on the amount of whitening and SPF protection desired in the final formulation. Preferably, the total amount of proprietary flavoring in the final product is from about 1% to about 10% by weight, more preferably about 1% to about 7% by weight. Preferably, the amount of sweetener added is an amount necessary to impart, in conjunction with the acid, a pleasing sour taste to the final composition that is similar to various commercially available sour candies. Typically, depending on the sweetener, this may be from about 0.05% to about 2.00% by weight.

There are various methods to manufacture the compositions of the present invention. As stated earlier, the acid is preferably dissolved in a solvent prior to being combined with the cosmetic base and other ingredients. To begin the process, a production vessel is filled with solvent and the requisite amount of acid is added to it. The mixture is agitated or stirred to effectuate mixing until the acid is completely dissolved in the solvent and forms a solution. Depending on the solvent, the solvent can be heated to facilitate dissolution of the acid. Typically, with the use of propylene glycol as the solvent, the solvent is heated to between about 80° and 90° C. and stirred for about 30 to 60 minutes. Once the acid is completely dissolved, the cosmetic lip base and other ingredients that are to be incorporated into the final composition are added to the solution. Preferably, the cosmetic base is added first and mixed thoroughly followed by the other ingredients. Depending on one's perspective, the solution can be thought of as being dissolved in the cosmetic base, or vice versa. Both expressions are synonymous as used herein, and refer to the combining of the two materials to form a substantially homogeneous mixture. The mixture is then stirred to completely dissolve the components and create a homogenous final composition. Depending on the actual ingredients used in a specific formulation, this composition may be a high quality suspension.

Depending on the exact composition of the cosmetic base and the concentration of ingredients, the final composition may have a consistency of anything from a conventional lipstick or hard wax to a thin cream. A typical composition according to the present invention will have a consistency similar to petrolatum or a thick cream with a viscosity of about 19560 centipoise as measured using a No. 4 spindle at 30 rpm and 25° C. and a specific gravity of about 0.88–0.92 g/ml. In this respect, a "doe-foot" applicator is useful in applying the composition. Although colorants may be added to the composition as described above to give the composition any color desired, added $TiO_2$ will give the composition an opaque white color that applies as a substantially clear layer on the lips in the absence of any added colorants.

EXAMPLES

The following examples are presented for the purpose of further illustrating the nature and scope of the present invention and are not intended as a limitation of the scope thereof. It should be appreciated that the present invention is in no way restricted to the following examples.

The formulation in table 1 lists the concentrations of the various ingredients, except for the flavor and a solubilizing agent, used to produce a bulk base for the samples produced according to Examples 1–6. The following formulation may be used no matter what flavor of product is being manufactured. The concentrations are in weight percent.

TABLE 1

Bulk Base Formulations for Samples in Examples 1–6

| Ingredient | Concentration (% w/w) | Supplier |
|---|---|---|
| Propylene Glycol USP | 7.00 | Vopak |
| Cosmetic Base[1] | 82.01 | Bonne Bell |
| White Beeswax | 2.75 | Strahl & Pitsch |
| Citric Acid USP | 5.33 | Vopak |
| Sodium saccharine (20% solution in propylene glycol) | 0.80 | Bonne Bell |
| Flavor Enhancer | 0.30 | Noville Inc. |
| Vitamin E | 0.50 | BASF |
| BV-OSC[2] | 0.01 | Barnet |
| $TiO_2$ | 0.10 | Bonne Bell |
| Timica 1500[3] | 1.20 | RONA |
| Lecinol S-10[4] | 0.30 | Barnet |
| Total | 100.00% | |

[1]Contains: petrolatum, polybutene, mineral oil, coconut oil, ozokerite, glycerin, trioctyldodecyl citrate, cetyl ricinoleate, shea butter extract, hydrogenated castor oil, mica, sorbitol, paraffin, propyl gallate, silica, propylparaben, butylparaben, aloe extract, ethylhexyl methoxycinnamate, tocopheryl acetate, buteth, and propylene glycol dipelargonate.
[2]Vitamin C in an oil solution
[3]Pearling agent
[4]Lecithin derived stabilizer The above-formulated composition may be considered a bulk base since, as stated, it may be used with any of the various flavored examples. Formulations of a final lip composition were produced using various flavors. These formulations are listed in Table 2 as examples 1–6.

TABLE 2

Final Lip Composition Formulations

| Ingredient | Supplier | 1 | 2 | 3 | 4 | 5 | 6 |
|---|---|---|---|---|---|---|---|
| Bulk Base | applicant | 93.80 | 93.80 | 94.25 | 95.05 | 94.30 | 94.05 |
| Grape flavor | FONA, #856. 193/WC | | | | | | 4.75 |
| Rasberry/Cherry flavor | Bell Flavors & Fragrances | | | | 0.75 | 4.50 | |
| Cotton Candy flavor | Wessel | | 5.00 | | 2.00 | | |
| Strawberry flavor | Arylessence | | | | 1.00 | | |
| Watermelon flavor | J. Manheimer | | | 4.55 | | | |
| Lemonade flavor | Custom Essence, CE14019 | 5.00 | | | | | |
| Solubilisant LRI[1] | Costec/LCW | 1.20 | 1.20 | 1.20 | 1.20 | 1.20 | 1.20 |

[1]Solubilizing agent for stabilizing frangrances

Obviously, the concentrations provided for the various ingredients of the bulk base in table 1 will change when combined with the flavor and Solubilisant LRI in the final composition. The new concentrations can be easily calculated. For example, the citric acid, which is present in a concentration of 5.33% by weight in the bulk base prior to the addition of flavor and solubilizing agent, will be present in a concentration of 5.00% by weight in a final composition formulated according to sample 1 (5.33×0.938=5.00).

A reaction vessel is filled with the amount of propylene glycol necessary to produce the specified concentration in the final composition. To this vessel, the acid and white beeswax are added in the specified amounts. The resulting mixture is heated to between about 80° and 90° C. with continuous stirring or similar agitation for about 30 to about 60 minutes until the acid and beeswax is completely dissolved and a liquid solution is achieved. Once the acid and wax are completely dissolved, the mixture is allowed to cool slightly to about 75 to 80° C. With the propylene glycol/acid/wax solution maintained at a temperature of between 75° and 80° C., the cosmetic lip base, which has been preheated to about 80 to 85° C., is added to the vessel with continued mixing. Once the cosmetic base has been added, the resultant mixture is maintained at a temperature of about 80° C. with continuous mixing. The heat is then removed and, with continued stirring, the mixture is allowed to cool. When the mixture reaches a temperature below about 70° C., the other ingredients listed in table 1 above are added to the mixture. The mixture is then stirred for an additional 1 to 4 hours until the mixture begins to thicken to the desired consistency as it continues to cool. The mixture is covered and allowed to sit at room temperature for about 6 to 24 hours. The mixture is then heated to about 65° C. with continuous stirring for approximately 1 to 3 hours to achieve a final smooth consistency. The bulk base product has an opaque white color and a consistency similar to a skin cream. This final bulk base may then be used to produce any flavor final lip composition desired.

To produce the final composition, the solubilisant LRI is heated in a separate tank to about 50° C. Once it is thoroughly heated, the flavor is added. This mixture is stirred thoroughly until it is a homogenous composition. The mixture is then added to the requisite amount of bulk base in a separate tank. The resulting composition is mixed for approximately 1.5 hours or until completely homogenous.

The invention has been described with reference to various preferred embodiments. Modifications and alterations will occur to others upon a reading and understanding of the specification. The invention is intended to include all such modifications and alterations insofar as they come within the scope of the appended claims and the equivalents thereof.

What is claimed is:

1. A composition for application on the lips, said composition comprising:
   a cosmetic base,
   an acid in a concentration of from about 2% to about 25% by weight of said total composition, and
   at least one of a sweetening agent and a flavoring agent.

2. A composition according to claim 1, further comprising a solvent that is miscible in said cosmetic base and in which said acid is miscible.

3. A composition according to claim 2, wherein said solvent is propylene glycol.

4. A composition according to claim 1, wherein said composition exhibits a pH of about 2.00–4.00.

5. A composition according to claim 4, wherein said composition exhibits a pH of about 2.68–3.90.

6. A composition according to claim 1, wherein said acid is present in a concentration of from about 2% to about 15% by weight of said total composition.

7. A composition according to claim 1, wherein said acid is one or more acids selected from the group consisting of citric acid, malic acid, tartaric acid, fumaric acid, propionic acid, acetic acid and lactic acid.

8. A composition according to claim 7, wherein said acid.

9. A composition according to claim 1, wherein said composition comprises both a sweetening agent and a flavoring agent.

10. A composition according to claim 1, wherein said flavoring agent is a fruit or candy flavored composition.

11. A composition according to claim 1, wherein said sweetening agent is a concentrated sweetener that exhibits a sweetness from 10 to 500 times greater than natural sugar.

12. A composition according to claim 1, wherein said composition includes one or more additives selected from the group consisting of oils, waxes, humectants, emollients, preservatives, antioxidants, emulsifiers, colorants, sunblocks, moisturizers, healing agents and vitamins.

13. A composition according to claim 1, wherein said cosmetic base includes polybutene and mineral oil.

14. A composition according to claim 1, wherein said cosmetic base is present in a concentration of from about 55% to about 90% by weight of said total composition.

15. A composition according to claim 14, wherein said cosmetic base is present in a concentration of from about 60% to about 85% by weight of said total composition.

16. A sour tasting composition for application on the lips, said composition comprising:
   one or more acids selected from the group consisting of citric acid, malic acid, tartaric acid, fumaric acid, propionic acid, acetic acid and lactic acid in a concentration of from about 2% to about 15% by weight of said total composition;

a solvent that is miscible in said cosmetic base and in which said acid is miscible in a concentration of from about 5% to about 20% by weight of said total composition; and a cosmetic base in a concentration of from about 60% to about 85% by weight of said total composition.

17. A composition according to claim 16, wherein said composition has a pH of about 2.00–4.00.

18. A process for forming a sour tasting composition suitable for application on the lips, said process comprising the steps of:

providing an acid;

dissolving said acid in a solvent to produce a solution; and subsequently dissolving a cosmetic base in said solution.

19. A process according to claim 18, wherein the step of dissolving said acid in said solvent is performed by adding said acid to said solvent at a temperature of between about 80° C. and 90° C. with continuous stirring.

20. A process according to claim 18, wherein the step of dissolving said cosmetic base in said solution is performed by adding said cosmetic base, heated to a temperature of about 80 to 85° C., to said solution with continuous mixing.

21. A process according to claim 18, further comprising the steps of:

stirring said composition for 2 to 4 hours after said cosmetic base is added to said solution;

subsequently allowing said composition to sit without stirring for about 6 to 24 hours; and then stirring said composition for 1 to 3 hours.

22. A process for forming a sour tasting composition suitable for application on the lips, said process comprising the steps of:

providing one or more acids selected from the group consisting of citric acid, malic acid, tartaric acid, fumaric acid, propionic acid, acetic acid and lactic acid;

dissolving said acids in a solvent at a temperature of between about 80° C. and 90° C. with continuous stirring to produce a solution, said solvent selected from the group consisting of propylene glycol, dipropylene glycol, butylene glycol, ethylene glycol, and glycerin;

adding a cosmetic base, heated to a temperature of about 80 to 85° C., to said solution with continuous stirring to form a mixture;

removing the heat from said mixture;

stirring said mixture for about 2 to 4 hours;

subsequently allowing said mixture to sit without stirring for about 6 to 24 hours; and then stirring said mixture for an additional 1 to 3 hours.

23. A composition according to claim 1, wherein said composition is substantially anhydrous.

24. A composition according to claim 6, wherein said acid is present in a concentration of about 5% by weight of said total composition.

* * * * *